United States Patent [19]

Lanier et al.

[11] Patent Number: 4,895,796
[45] Date of Patent: Jan. 23, 1990

[54] IDENTIFICATION OF NK CELLS AND CYTOTOXIC T LYMPHOCYTES

[75] Inventors: Lewis L. Lanier, Los Altos; Joseph H. Phillips, San Mateo; Anne L. Jackson, Sunnyvale, all of Calif.

[73] Assignee: Becton Dickinson and Company, Franklin Lakes, N.J.

[21] Appl. No.: 141,626

[22] Filed: Jan. 6, 1988

[51] Int. Cl.$^4$ .................. G01N 33/569; G01N 33/577
[52] U.S. Cl. .......................................... 435/7; 435/34; 436/548; 436/800; 530/391; 530/809; 935/110
[58] Field of Search ...................... 435/7, 34; 436/548, 436/800; 530/391, 808, 809; 935/110

[56] References Cited

U.S. PATENT DOCUMENTS 4,599,304 7/1986 Lanier et al. .................... 436/548
4,772,552 9/1988 Hercend et al. .................. 436/548

OTHER PUBLICATIONS

Lanier et al, *Journ. Immunol.*, 136, 4480–4486, 1986.

*Primary Examiner*—Robert J. Warden
*Assistant Examiner*—David A. Saunders
*Attorney, Agent, or Firm*—Richard L. Neeley

[57] ABSTRACT

A method for distinguishing between NK cells and T lymphocytes is provided, which comprises contacting a sample containing lymphocytes with a first reagent comprising anti-CD3 and a first detectable label and a second reagent comprising a mixture of anti-CD16 and anti-GP160 (Leu-19) both labeled with a second detectable label, and identifying cells that react with the reagents, whereby cells that react with the first reagent are identified as T lymphocytes, and cells that react only with the second reagent are identified as NK cells. Cells that react with both reagents are identified as a unique subset of T lymphocytes some of which may mediate MHC unrestricted cytolysis.

17 Claims, 1 Drawing Sheet

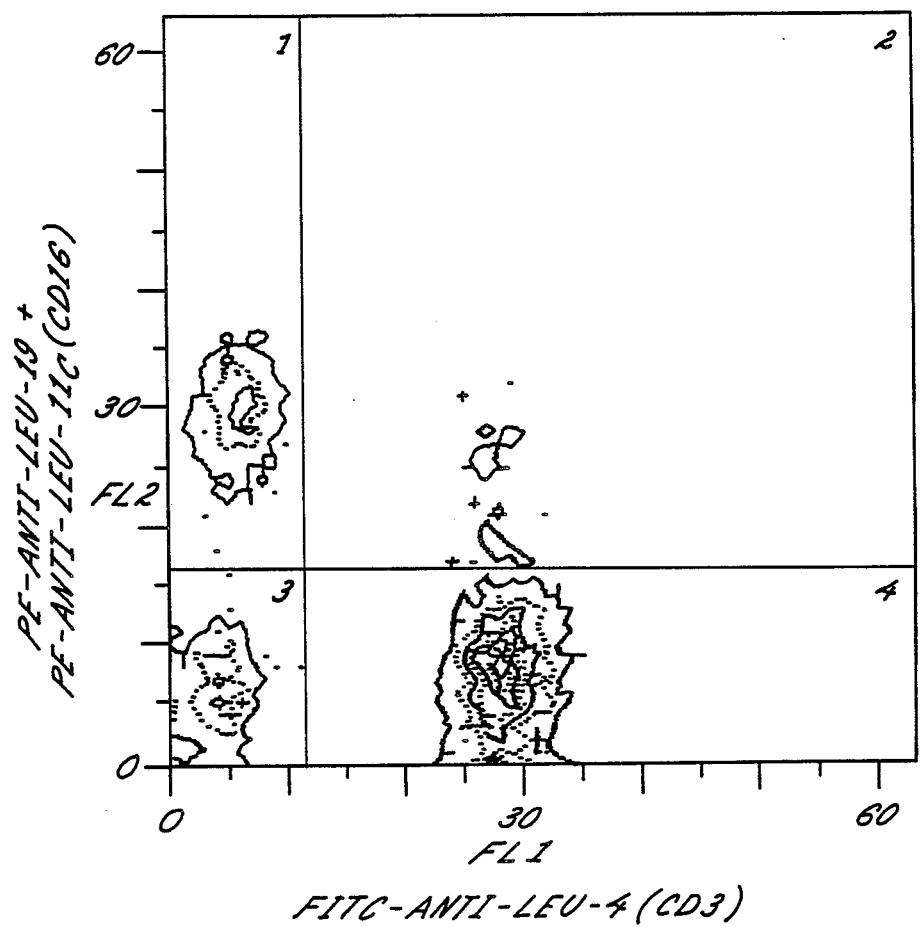
FIGURE

IDENTIFICATION OF NK CELLS AND CYTOTOXIC T LYMPHOCYTES

FIELD OF THE INVENTION

This invention relates to the fields of immunology and cell analysis and is particularly directed to techniques for distinguishing between classes of human lymphocytes.

BACKGROUND OF THE INVENTION

Lymphocytes are a subset of leukocytes (white blood cells). Within the lymphocyte population, at least two distinct cell types have been identified that are able to lyse other cells, including autologous malignant cells, autologous virus-infected cells, and allogeneic cells. These two predominant cytotoxic lymphocytes are cytotoxic T lymphocytes (CTL) and natural killer (NK) cells.

All T lymphocytes, including CTL, express on the plasma membrane and/or in the cytoplasm an antigen referred to as CD3, along with numerous other antigens that are associated with various T-cell subtypes. CD3 is composed of at least three proteins of 20-30 kD that are non-covalently associated with the T-cell-antigen receptor (i.e., the structure responsible for antigen recognition). Numerous antibodies have been produced against CD3, including the anti-Leu-4 monoclonal antibody (commercially available from Becton Dickinson Monoclonal Center, Inc.). Most CTL lyse target cells (for example, virus-infected target cells) provided that the target cells express syngeneic major histocompatability (MHC) antigens. Accordingly, such cells are subject to MHC restriction.

NK cells differ from T lymphocytes in that most NK cells do not express either CD3 antigen or the T-cell-antigen receptor (see Lanier et al., *J. Immunol.* (1986) 137:2735). NK cells are also able to lyse certain tumor cells and virus-infected cells, but are not MHC restricted.

Whereas T cells can be readily identified by their reactivity with anti-CD3 antibodies, there has been no simple and sensitive method for the identification or enumeration of NK cells using a single labeling reagent. It is well known that most NK cells express the CD16 antigen. CD16 is a 50-70 kD glycoprotein that is associated with a receptor for IgG. Numerous antibodies have been produced against CD16, including anti-Leu-11a, VEP13, B73.1, L23 and others (Lanier et al., *J. Immunol.* (1983) 131:1789; Perussia et al., *J. Immunol.* (1983) 130:2133; Perussia et al., *J. Immunol.* (1983) 130:2142; Rumpold et al., *J. Immunol.* (1982) 129:1458; Lanier et al., *J. Immunol.* (1986) 136:4480). However, it has been demonstrated that CD16 cannot be detected on all NK cells, particularly NK cells that have been activated in culture. Moreover, in certain circumstances CD16 can also be expressed on T lymphocytes (Lanier et al., *J. Exp. Med.* (1985) 162:2089). Most NK cells express another glycoprotein on the plasma membrane that is identified by the anti-Leu-19 monoclonal antibody, an antibody commercially available from the Becton Dickinson Monoclonal Center, Inc. Anti-Leu-19 recognizes a glycoprotein of about 160 kD (GP160) that is also recognized by the NKH-1 monoclonal antibody (Lanier et al., *J. Immunol.* (1986) 136:4480). However, neither anti-Leu-19 nor NKH-1 react exclusively with NK cells but can also react with other non-lymphocyte cell types (Lanier et al., *J. Immunol.* (1987) 138:2019). Anti-Leu-19 also reacts with a unique minor subset of T lymphocytes, at least some of which kill without MHC restriction (Lanier et al., *J. Immunol.* (1986) 136:4480). Finally, the amount of the antigen recognized by anti-Leu-19 on the plasma membrane of NK cells is often low, making it difficult to precisely identify and enumerate the number of NK cells in a mixed cell population, such as blood or other tissues.

Recently, a new method of cancer therapy has been developed that involves the combined use of in vivo interleukin-2 (IL-2) drug treatment and administrating the patient's autologous lymphocytes that have been activated in vitro with IL-2, often referred to as lymphokine-activated killer (LAK) cell and IL-2 therapy (Rosenberg et al., *N. Eng. J. Med.* (1985) 313:1485). There is evidence that the cytotoxic effector cells are predominantly NK cells (Phillips and Lanier, *J. Exp. Med.* (1986) 164:814). Thus, there is a clear need for a method to identify, enumerate, and monitor the levels of NK cells and T lymphocytes in this type of therapy, as well as in other clinical situations to evaluate activation or suppression of the immune system.

Prior to the present invention unequivocal simultaneous identification of NK cells and T lymphocytes was not possible using a single assay. Accordingly, there remains a need for distinguishing between NK cells and T cells using techniques that can be simpilifed and, in preferred embodiments, automated.

SUMMARY OF THE INVENTION

The present invention provides a method for distinguishing between NK cells and cytotoxic T lymphocytes, which comprises contacting a sample containing lymphocytes with a first reagent comprising anti-CD3 and a first detectable label and a second reagent comprising a mixture of anti-CD16 and anti-GP160 both labeled with a second detectable label, and distinguishing cells that react with said first reagent from cells that react with said second reagent, whereby cells that react only with said first reagent are identified as T lymphocytes and cells that react only with said second reagent are identified as NK cells. Lymphocytes reacting with both reagents are identified as a unique subpopulation of T lymphocytes, some of which may mediate MHC unrestricted cytolysis. In preferred embodiments the two reagents are conjugated with different fluorophores, and the cells are detected by microscopy or flow cytometry.

BRIEF DESCRIPTION OF THE DRAWING

The invention will be better understood by reference to the following detailed description of specific embodiments when considered in conjunction with the FIGURE that forms part of the present specification, wherein:

The FIGURE is a graph showing the fluorescence of cells labeled with FITC-anti-Leu-4 (CD3) versus fluorescence of cells labeled with PE-anti-Leu-19 (GP160) plus PE-anti-Leu-11c (CD16).

DETAILED DESCRIPTION OF SPECIFIC EMBODIMENTS

In accordance with the present invention, NK cells and cytotoxic T lymphocytes can be distinguished from one another on the basis of cell surface antigens. These cell surface antigens are recognized by the ability of labeled antibodies specific for these antigens to bind with the cell surfaces. When an unknown mixture of cells containing lymphocytes is contacted with a mixture of the reagents of the invention, T lymphocytes, NK cells, and certain other classes of cells can be recognized by the different manner in which the two reagents bind to the cells. The first reagent comprises an anti-CD3 antibody while the second reagent comprises a mixture of antibodies (anti-CD16 and anti-GP160). The two reagents are labeled with different detectable labels that allow them to be differentiated. Cells that react with the first reagent are identified as T lymphocytes, cells that react solely with the second agent are identified as NK cells, and cells that react with both reagents form a subset of T lymphocytes, some of which mediate non-MHC restricted cytotoxic functions.

Cell surface antigens on lymphocytes and NK cells have been identified using several systems of nomenclature. For example, the antigen identified as Leu-4 in this specification is also known as the CD3 antigen using the CD nomenclature for differentiation antigens. Similarly, the Leu-11 antigen is known as CD16. The relationship of the antigen recognized by anti-Leu-19 to the CD cluster antigens has not been established, but the Leu-19 antigen appears to be the same as the antigen identified by the NKH-1 antibody. For the purposes of this application, this third antigenic material is referred to as GP160. The CD and GP160 designations refer to the entire antigen and are more general than the Leu designations, which are derived from a series of monoclonal antibodies that recognize specific determinants on the antigens. In some instances in this discussion of the invention, reference is made to the Leu designations while in other instances the more general CD and GP160 designations are used. While in some instances it will be clear from the context that either the general or the specific case is intended, in many cases the two terms are used interchangeably.

The Leu system of nomenclature arose from the use of monoclonal antibodies that reacted specifically with individual antigens present on the surface of cells. Anti-Leu-4 reacts with CD3, a complex of at least three proteins of 20-30 kD (Kan et al., *J. Immunol.* (1983) 131:536; Borst et al., *J. Immunol.* (1982) 128:1560). Anti-Leu-11 specifically reacts with the CD16 antigen. CD16 is a 50,000–70,000 Dalton protein that is associated with the Fc receptor for IgG present on NK cells and neutrophils. For a detailed discussion of the antigen and its reactivity, see, for example, Lanier et al., *J. Immunol.* (1983) 131:1789; Perussia et al., *J. Immunol.* (1983) 130:2133; Perussia et al., *J. Immunol.* (1983) 130:2142; Rumpold et al., *J. Immunol.* (1982) 129:1458; and Perussia et al., *J. Immunol.* (1984) 133:180. GP160, the antigen recognized by anti-Leu-19, is a glycoprotein with a molecular weight of about 160,000 Daltons and an unknown function. For a detailed description of its properties and reactivity, see, for example, Lanier et al., *J. Immunol.* (1986) 136:4480; Griffin et al., *J. Immunol.* (1983) 130:2947 and Hercend, *J. Clin. Invest.* (1985) 75:932. GP160 has not yet been given a CD name by the Leukocyte Differentiation Antigen Workshop Committee of the World Health Organization. Note that in prior reports the molecular weight was overestimated; more recent studies indicate that the relative mobility is approximately 160,000 kD.

Monoclonal antibodies useful in the practice of the present invention can be prepared by standard techniques as descried below. Anti-Leu-11 can be produced by immunizing mice with human peripheral blood, low-buoyant-density lymphocytes or granulocytes and fusing the immune splenocytes with a myeloma cell line. The antigenic specificity for Leu-11 in the resulting hybridomas can be determined by competitive binding studies and immunoprecipitation of the CD16 antigen. Anti-Leu-19 can be prepared in a similar manner by immunizing mice with the KG1a cell line (Koeffler et al., *Blood* (1980) 61:1222), fusing the immune splenocytes with a myeloma cell line, and selecting cells that produce an antibody reactive with the NKH-1 antigen. Anti-Leu-4 can be produced by immunizing mice with human thymocytes or peripheral T lymphocytes, fusing the immune splenocytes with myeloma cell line, and selecting cells that produce an antibody reactive with CD3. Antigenic specificity can be determined by competitive binding studies and immunoprecipitation of CD3 antigen (Beverly and Callard, *Eur. J. Immunol.* (1981) 11:329; Kung et al., *Science* (1979) 206:347).

The specific monoclonal antibodies set forth herein or their equivalent can be used in the practice of this invention. The monoclonal antibodies can belong to any of the classes or subclasses of antibodies, including IgA, IgD, IgE, IgG (subclasses 1-4, if human; 1, 2a, 2b, 3 if murine), or IgM. Actively binding fragments of the antibodies can be employed, such as Fab, $F(ab')_2$, or the like. The monoclonal antibodies can be prepared by any convenient means which provides immortalization of the B-lymphocyte genes encoding the antibody subunits or Fv, such as fusion between sensitized lymphocytes and a myeloma fusion partner; transformation, e.g., with EBV; or other immortalization technique. Alternatively, the genes can be isolated from a lymphocytic host expressing the antibodies and transferred to a more convenient host for expression in accordance with known genetic engineering techniques.

The antibodies may be obtained from any convenient vertebrate source, such as rodent (e.g., mouse, rat), primate (e.g., human), lagomorpha, bovine, ovine, equine, porcine, etc. The antibodies are often prepared by fusing spleen or other tissue cells from a host with myeloma cells in accordance with known techniques or by transforming the spleen cells with an appropriate transforming vector to immortalize the cells. The cells can be cultured in a selective medium and screened to select antibodies that bind the designated antigens.

For diagnostic assays, the antibodies can be labeled using standard techniques. A wide variety of labels are known which provide for a detectable signal. Illustrative labels include radioisotopes, e.g., $^3H$, $^{125}I$, $^{131}I$, and $^{14}C$; fluorescers, e.g., fluorescein, phycobiliproteins, rare earth chelates, and rhodamine; enzyme substrates and inhibitors; enzymes, such as horseradish peroxidase, glucose oxidase, glucose-6-phosphate dehydrogenase, $\beta$-galactosidase, and acetylcholinesterase; or particles, e.g., dextran, agarose, metal particles, carbon, magnetic particles, or polystyrene particles. Methods for conjugating labels to proteins have found extensive description in the literature; see, for example, U.S. Pat. Nos. 3,817,837; 4,134,792; and 4,220,722.

The labeling employed will follow conventional techniques, and the number of labels per antibody will vary depending upon the nature of the label, the sensitivity of the signal desired, and the like. Numerous assay protocols have been developed for use with antibodies for the detection of a wide variety of analytes which are applicable here. See, for example, U.S. Pat. Nos. 3,791,932; 3,817,837; 4,134,792; 4,174,384; 4,275,149;

and 4,299,916, which are incorporated herein by reference.

It is particularly preferred to use two different fluorescent labels as the first and second label used in the method of the invention. Use of different fluorescent labels allows easy detection and cell sorting by flow cytometry using automated equipment. A preferred pair of fluorescent labels is fluorescein (conjugated from the isothiocyanate, FITC) and phycoerythrin (conjugated to the antibody with SPDP, which is N-succinimidyl-3-(2-pyridyldithio)propionate). Other suitable cross-linkers and coupling techniques for attaching fluorophores to antibodies can be used. Either fluorescein or phycoerythrin can be used as the first detectable label with the other being used as the second detectable label as long as one label is used with anti-Leu-4 and the other label used for both anti-Leu-11 and anti-Leu-19.

Once labeled reagents are available, the labeled reagents are contacted with lymphocytes whose type is being determined in a reaction medium in which antibody binding can take place. The reaction medium is typically an aqueous suspension of cells containing a buffer that maintains the solution in the acceptable physiological range of parameters (e.g., temperature, pH, and osmolarity) for the particular type of cell being analyzed.

T lymphocytes and NK cells are distinguished by their ability to bind with the two reagents. All cells which react with anti-Leu-4 are identified as T lymphocytes whether or not they also react with anti-Leu-11 and/or anti-Leu-19. Those cells which react with both anti-Leu-4 (Reagent 1) and anti-Leu-19 or anti-Leu-11 (Reagent 2) form a subset of T lymphocytes, some of which mediate non-MHC restricted cytotoxic function. Lymphoid cells which react with Reagent 2 (anti-Leu-11 and/or anti-Leu-19) but not with Reagent 1 (anti-Leu-4) are identified as NK cells.

The method used to detect differences between the two cell types will naturally vary with the types of labels used. For example, different radioactive labels can be distinguished by use of a differential radiation detector (e.g., a gamma counter capable of distinguishing isotopes based on their radiation spectrums). Use of two different fluorescent labels is particularly preferred as fluorescent labels allow cells to be detected and if desired sorted automatically using flow cytometry. Fluorescence-activated cell sorters (FACS) are commercially available flow cytometers and are capable of distinguishing between cells labeled in the manner described.

In some cases, the purpose of detecting the different cell types will be diagnostic. For example, a new method of cancer therapy has been developed that involves the combined use of in vivo interleukin-2 (IL-2) drug treatment and re-infusing the patient's autologous lymphocytes that have been activated in vitro with IL-2, often referred to as lymphokine-activated killer (LAK) cell and IL-2 therapy (Rosenberg et al., *N. Eng. J. Med.* (1985) 313:1485). There is evidence that the cytotoxic effector cells are predominantly NK cells (Phillips and Lanier, *J. Exp. Med.* (1986) 164:814). Thus, there is a clear need for a method to identify, enumerate, and monitor the levels of NK cells and T lymphocytes in this type of therapy. In this situation, it is clearly advantageous to use the simple assay described in this invention. By using a combination of both PE conjugated anti-CD16 and anti-GP160, in conjunction with FITC anti-CD3, this invention allows identification of substantially all NK cells, which will be stained with PE, but not FITC dye. The invention also allows simultaneous detection of T lymphocytes, identified as cells stained with FITC but not PE, and the detection of unique T cells that express both (1) CD3 and (2) CD16 and/or GP160, which includes a population of T cells that mediate MHC unrestricted cytotoxicity. The invention is also useful in determining the immune status of patients, in that it permits simultaneous determination of the total numbers and percentages of NK and T cells. This can be compared to normal values in order to determine whether the proportions or absolute number of these cell types are normal or abnormal in certain disease states. Another application of this assay will be to potentially detect a lymphoproliferative disorder in which the unique T cell population expressing (1) CD3 and (2) CD16 and/or GP160 are significantly elevated over normal values (Reynolds and Foon, *Blood* (1984) 64:1146).

The invention now being generally described, the same will be better understood by reference to the following examples which are provided for purposes of illustration only and are not intended to be limiting of the invention unless so specified.

EXAMPLES

Example 1

Preparation of Monoclonal Antibodies

Anti-Leu-11d monoclonal antibody (MAb) was produced by a hybridoma cell line identified as L23. L23 was derived by immunizing BALB/c mice with human peripheral blood low buoyant density lymphocytes and fusing the immune spleenocytes with the SP2/0 myeloma cell line. The L23 hybridoma produces an IgG1, κ MAb. An IgG2a isotype-switch variant designated L23b was selected by fluorescence-activated cell sorting by using fluorescein isothiocyanate (FITC)-conjugated goat anti-mouse IgG2a-specific antiserum (Southern Biotech, Birmingham Al.). The antigenic specificity (anti-Leu-11d) was determined by competitive binding studies and immunoprecipitation of the CD16 antigen.

Anti-Leu-19, an IgG1, κ MAb, was produced by the My31 hybridoma cell line. My31 was derived by immunizing (C57BL/6 x BALB/c) $F_1$ mice with the KG1a cell line (described in Koeffler et al., *Blood* (1980) 61:1222), fusing the immune spleenocytes with the SP2/0 myeloma cell line, and selecting for antigenic specificity using the indicated antigen.

Anti-Leu-4 was produced by the SK7 hybridoma cell line. SK7 was derived by immunizing BALB/c mice with human thymocytes, fusing the immune spleenocytes with the NS-1 myeloma cell line, and selecting for antibodies reactive with T lymphocytes.

Fluorescent Labeling

The following general procedure was used to conjugate fluorescein isothiocyanate to an antibody.

Purified antibody was normally stored in the presence of azide as an antibacterial. In order to remove the azide, which interferes with the coupling reaction, the antibody at about 1 mg/ml antibody concentration was dialyzed extensively into bicarbonate/carbonate buffer at pH 9.0–9.5. The resulting solution was mixed will and the pH checked to ensure that it was in the range from 9.0–9.5. A fresh stock solution of FITC was prepared containing an amount of fluorophore based on the total number of milligrams of antibody being labeled and the ratio of micrograms of FITC to milligrams of protein desired, typically around 100 μg/mg Ab. FITC was initially dissolved in DMSO (dimethylsulfoxide) in an amount selected to ensure that the amount of DMSO in the FITC solution initially added to the protein solution in the coupling step is less than 5% by volume. FITC in DMSO was added dropwise with stirring to the antibody solution until a final concentration of about 100 μg FITC per mg Ab was achieved.

After the reagents were mixed, the reaction tube was covered with foil or kept in the dark while incubating for 2 hours at room temperature. At the end of 2 hours, the reaction mixture was passed through a desalting column to separate the conjugated antibody from the unconjugated FITC. The desalting gel used was a Sephadex G-25 medium equilibrated with 1X PBS at room temperature. The gel volume was approximately 5-10 times the volume of the reaction mixture.

The conjugated antibody elutes in the first colored band. All of this band was collected and pooled. The pooled antibody was dialyzed into a buffer selected for the particular antibody for at least $10^4$ volume changes while being protected from light. Sufficient $NaN_3$ was added to achieve a final concentration of 0.1% $NaN_3$ in the storage solution.

The procedure set forth above was used to label anti-Leu-4 which was used in the assay described below.

Conjugation of monoclonal antibody with phycoerythrin can be performed as described by the standard method described by Hardy (Purification and coupling of fluorescent proteins for use in flow cytometry, In: Handbook of Experimental Immunology, 4th ed., Volume 1, Chapter 31, ed., L.A. Herzenberg et al., Blackwell Scientific Publications, Oxford, UK, 1986).

Sample Analysis

Human peripheral blood from random normal donors was obtained from a blood bank. Mononuclear cells were isolated by using Ficoll/Hypaque by standard techniques.

Immunofluorescence was measured and flow cytometry carried out using standard techniques, described in, for example, Lanier et al., *J. Immunol.* (1983) 131:1789 and Parks et al., "Flow cytometry and fluorescence activated cell sorting (FACS)" in *Handbook of Experimental Immunology*, 4th Ed., Weir et al., Eds., Blackwell Publications, Ltd., Edinburgh, UK, 1986.

The ability of the first and second reagents of the invention to distinguish T cells from NK cells was compared to the use of more conventional methods for detecting T and NK cells. The present invention has several advantages compared to the more conventional method of enumeration of T cells and NK cells:

1. Use of a single PE anti-Leu-19 (GP160) reagent overestimates the proportion of NK cells, since some T cells can express Leu-19. By combining PE anti-Leu-19 with FITC anti-Leu-4 (CD3), it is possible to identify the unique T cells expressing both CD3 and Leu-19, and to more precisely enumerate the NK cells that stain with PE anti-Leu-19 but not FITC anti-CD3.

2. Use of a single PE anti-CD16 (Leu-11) reagent can overestimate the proportion of NK cells in a population. In some individuals, some T cells express CD16. By combining PE anti-Leu-11 with FITC anti-Leu-4 (CD3), it is possible to identify the unique T cells expressing both CD3 and Leu-11, and to more precisely enumerate the NK cells that stain with PE anti-Leu-11 but not FITC anti-CD3.

3. Use of a single PE anti-CD16 (Leu-11) reagent can also underestimate the proportion of NK cells in a population. A population of NK cells in normal blood, as well as some activated NK cells, do not express CD16. However, these CD16 negative NK cells have been shown to express Leu-19. Therefore, by mixing PE conjugated anti-Leu-11 and PE anti-Leu-19 and using this mixed PE conjugated antibody combination in conjunction with the FITC anti-CD3, it is possible to identify substantially all NK cells, including both CD16-,Leu-19+ and CD16+,Leu-19+ NK cells. Using this novel combination of reagents, it is possible to simultaneously identify and enumerate total T cells (CD3+cells), unique T cells expressing either CD16 and/or Leu-19, and total NK cells (CD3-, Leu-19+ and-/or CD16+cells).

4. Another major advantage in the present invention relates to sensitivity of detection of NK cells. The majority of NK cells in normal tissues express both CD16 and Leu-19. The combined use of both PE conjugated antibodies results in the binding of both antibodies to the plasma membrane of a majority of NK cells. This results in brighter staining of the majority of NK cells, hence, better sensitivity in the assay.

An illustration of peripheral blood mononuclear cells stained with a first reagent of the invention (FITC conjugated anti-Leu-4 (CD16)) and a second reagent of the invention (consisting of a mixture of PE conjugated anti-Leu-11 (CD16) and PE conjugated anti-Leu-19) is presented in the FIGURE. Samples were analyzed by flow cytometry, and correlated fluorescence of the lymphocyte fraction of mononuclear cells is shown as a contour plot. The display is divided into quadrants. Unstained cells (non-T, non-NK cells) are present in the lower left quadrant, NK cells are present in the upper left quadrant (stained with PE anti-Leu-11 and/or Leu-19, but not FITC anti-Leu4), T cells are present in the lower right quadrant (stained with FITC anti-Leu-4, but not PE anti-Leu-11 or Leu-19), and the unique Leu-11 and/or Leu-19 positive T cells are present in the upper right quadrant (stained with both FITC and PE dyes).

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for distinguishing between substantially all NK cells and all T lymphocytes, which comprises:
   contacting a sample containing lymphocytes with a first reagent comprising anti-CD3 and a first detectable label and a second reagent comprising a mixture of anti-CD16 and anti-GP160 both labeled with a second detectable label; and
   identifying cells that react with said reagents wherein cells that react with said first reagent are identified as all of the population of T lymphoctyes, and cells that react with said second reagent but not with said first reagent are identified as substantially all of the population of NK cells.

2. The method of claim 1, wherein cells that react with both said first reagent and said second reagent are identified as a subset of T lymphocytes comprising cells that mediate major-histocompatibilitycomplex-unrestricted cytolysis.

3. The method of claim 1, wherein anti-CD3 is anti-Leu-4 monoclonal antibody.

4. The method of claim 1, wherein anti-CD16 and anti-GP160 are anti-Leu-11 and anti-Leu-19 monoclonal antibodies, respectively.

5. The method of claim 1, wherein said first detectable label is a fluorescent label and said second detectable label is a different fluorescent label having an emission spectrum distinguishable from that of said first fluorescent label.

6. The method of claim 5, wherein said identifying comprises visually examining said sample microscopically.

7. The method of claim 5, wherein said identifying comprises electronically detecting said cells using a flow cytometer.

8. The method of claim 1, wherein both reagents are contacted simultaneously with said sample.

9. The method of claim 1, wherein the sample comprises blood, erythrocyte-depleted whole blood, the mononuclear cell fraction of whole blood, lymphocytes isolated from a solid lymphoid tissue, bone marrow cells, or lymphoid cells infiltrating tumors.

10. The method of claim 9, wherein said solid lymphoid tissue is thymus, lymph node, or spleen tissue.

11. A reagent mixture for identifying substantially all NK cells, said mixture comprising:
anti-CD16 and anti-GP160 labeled with the same detectable label.

12. The reagent mixture of claim 11, wherein said mixture further comprises anti-CD3 labeled with a different detectable label distinguishable from said same detectable label of anti-CD16 and anti-GP160.

13. The reagent mixture of claim 12, wherein said detectable labels are fluorophores.

14. The reagent mixture of claim 13, wherein said detectable labels are fluorescein and phycoerythrin.

15. The reagent mixture of claim 11, wherein said anti-CD16 is monoclonal anti-Leu-11.

16. The reagent mixture of claim 11, wherein said anti-GP160 is monoclonal anti-Leu-19.

17. The reagent mixture of claim 11, wherein said anti-CD3 is monoclonal anti-Leu-4.

* * * * *